United States Patent [19]  [11] Patent Number: 4,891,428
Nordhoff et al.  [45] Date of Patent: * Jan. 2, 1990

[54] IMIDAZOLINYL DERIVATIVES, HAVING HERBICIDAL ACTIVITY

[75] Inventors: Erhard Nordhoff; Wilfried Franke; Friedrich Arndt, all of Berlin, Fed. Rep. of Germany

[73] Assignee: Schering Aktiengesellschaft, Berlin and Bergkamen, Fed. Rep. of Germany

[*] Notice: The portion of the term of this patent subsequent to Oct. 11, 2005 has been disclaimed.

[21] Appl. No.: 220,368

[22] Filed: Jul. 11, 1988

Related U.S. Application Data

[63] Continuation of Ser. No. 911,004, Sep. 24, 1986, Pat. No. 4,776,876.

[30] Foreign Application Priority Data

Sep. 24, 1985 [DE] Fed. Rep. of Germany ....... 3534391
Feb. 17, 1986 [DE] Fed. Rep. of Germany ....... 3605343

[51] Int. Cl.⁴ ........................................... C07D 401/04
[52] U.S. Cl. .................................. 546/278; 546/256; 71/92
[58] Field of Search ........................... 546/278, 15, 256

[56] References Cited

U.S. PATENT DOCUMENTS 4,404,012 9/1983 Orwick et al. ...................... 546/278
4,647,301 3/1987 Los ..................................... 546/278

Primary Examiner—Jane T. Fan
Attorney, Agent, or Firm—Michael J. Striker

[57] ABSTRACT

New 2-(2-imidazolin-2-yl)-pyridin-3-carboxylic acid derivatives are disclosed, of the general formula (I)

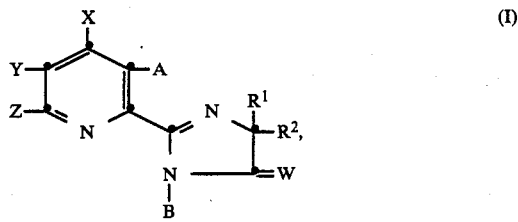

processes for the production of these compounds, as well as compositions containing the same, having herbicidal activity.

1 Claim, No Drawings

IMIDAZOLINYL DERIVATIVES, HAVING HERBICIDAL ACTIVITY

This is a continuation of application Ser. No. 911,004, filed Sept. 24, 1986, now U.S. Pat. No. 4,776,876, issued Oct. 11, 1988.

BACKGROUND OF THE INVENTION

The invention concerns new imidazolinyl derivatives, processes for the production of these compounds, as well as their employment in compositions having herbicidal activity.

It is already known that imidazolines possess herbicidal characteristics (see, e.g. German Offenlegungsschriften DE-OS 28 33 274 and DE-OS 31 21 736). However, the herbicidal activity of these is frequently not sufficient, or there occur, with otherwise appropriate herbicidal activity, problems of selectivity in agricultural main cultures.

It is therefore an object according to the present invention to prepare new compounds which do not display these disadvantages, and which surpass the previously known compounds with respect to their biological characteristics.

SUMMARY OF THE INVENTION

It has been discovered that 2-(2-imidazolin-2-yl)-pyridin-3-carboxylic acid derivatives of the general formula I:

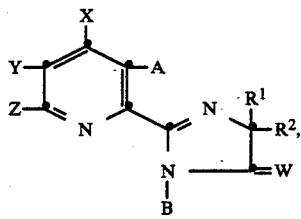

in which
$R^1$ is $C_1-C_4$-alkyl,
$R^2$ is $C_1-C_4$-alkyl or $C_3-C_6$-cycloalkyl or $R^1$ and $R^2$ together with the adjacent carbon atom are $C_3-C_6$-cycloalkyl, if necessary substituted by methyl,
W is an oxygen or sulfur atom,
A is one of the groups $CH_2OH$, $COOR^3$ or $CONR^4R^5$,
$R^3$ is hydrogen, $C_1-C_{12}$-alkyl, if necessary interrupted by one or more oxygen or sulfur atoms and if necessary substituted by $C_1-C_3$-alkoxy, halogen, hydroxy, $C_3-C_6$-cycloalkyl, benzyl, furyl, tetrahydrofuryl, phenyl, halogenphenyl, $C_1-C_4$-alkylphenyl, $C_1-C_4$-alkoxyphenyl, nitrophenyl, cyano, carboxyl, $C_1-C_4$-alkoxycarbonyl or $C_1-C_4$-alkylthio, $C_3-C_8$-alkenyl, if necessary substituted by $C_1-C_3$-alkoxy, halogen or phenyl, $C_3-C_8$-alkinyl, if necessary substituted by $C_1-C_3$-alkoxy, phenyl or halogen, $C_3-C_6$-cycloalkyl, if necessary substituted by methyl, or a cation of the group of alkali metals, earth alkali metals, manganese, copper, iron, zinc, ammonium and organic ammonium compounds, $R^4$ and $R^5$ are, independently from one another, hydrogen, hydroxy or $C_1-C_4$-alkyl, and for the case in which $R^4$ is hydrogen, $R^5$ is also amino, dimethylamino, acetylamino or anilino, X is hydrogen, nitro, $C_1-C_3$-alkyl, $C_1-C_3$-halogenalkyl, or $C_1-C_3$-alkoxy, and
one of both Y and Z is one of the groups $SR^6$ or $OR^7$ while the other of Y and Z is hydrogen, halogen, $C_1-C_4$-alkyl, $C_1-C_4$-halogenalkyl, $C_1-C_4$-alkoxy or $C_1-C_4$-alkylthio, $R^6$ is hydrogen, phenyl, halogenphenyl, $C_1-C_3$-alkylphenyl, di-$C_1-C_3$-alkylphenyl, nitrophenyl, $C_1-C_3$-alkoxyphenyl, pyridyl, $C_1-C_3$-alkylpyridyl, $C_2-C_8$-alkyl interrupted one or more times by oxygen, $C_3-C_8$-cycloalkyl, if necessary interrupted by oxygen, sulfur, imino or $C_1-C_4$-alkylimino and if necessary substituted one or more times by $C_1-C_4$-alkyl, $C_1-C_4$-alkoxy or halogen, $C_5-C_8$-cycloalkenyl or $C_1-C_{12}$-alkyl, $C_3-C_{12}$-alkenyl or $C_3-C_{12}$-alkinyl if necessary substituted one or more times by cyano, halogen, mydroxy, mercapto, amino, $C_1-C_6$-alkoxy, $C_1-C_4$-alkylthio, carboxyl, carbamoyl, $C_1-C_4$-alkoxycarbonyl, $C_1-C_4$-alkylthiocarbonyl, oxo, thioxo, di-$C_1-C_3$-alkoxy, hydroxyimino, $C_3-C_8$-cycloalkyl, $C_3-C_8$-cycloalkenyl, phenyl, halogenphenyl, $C_1-C_3$-alkylphenyl, nitrophenyl, $C_1-C_3$-alkoxyphenyl, furyl, tetrahydrofuryl, dioxolanyl, $C_1-C_6$-alkylamino, $C_3-C_8$-cycloalkylamino, pyridyl, $C_1-C_4$-alkylpyridyl, pyrrolidinyl, piperidinyl, N-$C_1-C_4$-alkylpiperidinyl $C_1-C_4$-alkylcyclopropyl, di-$C_1-C_4$-alkyl-dioxolanyl, $R^7$ is hydrogen, $C_3-C_8$-cycloalkyl, if necessary interrupted by oxygen, sulfur, imino or $C_1-C_4$-alkylimino and if necessary substituted one or more times by $C_1-C_4$-alkyl, $C_1-C_4$-alkoxy or halogen, $C_5-C_8$-cycloalkenyl, or $C_1-C_{12}$-alkyl-, $C_3-C_{12}$-alkenyl- or $C_3-C_{12}$-alkinyl- if necessary substituted one or more times by cyano, hydroxy, mercapto, amino, hydroxy-$C_1-C_6$-alkyl, $C_1-C_6$-alkoxy, $C_1-C_4$-alkylthio, carboxyl, carbamoyl, acetyl, $C_1-C_4$-alkoxycarbonyl, $C_1-C_4$-alkylthiocarbonyl, oxo, thioxo, di-$C_1-C_3$-alkoxy, hydroxyimino, $C_3-C_8$-cycloalkyl, dioxolanyl, $C_5-C_8$-cycloalkenyl, furyl, tetrahydrofuryl, $C_1-C_6$-alkylamino, $C_3-C_8$-cycloalkylamino, di-$C_1-C_6$-alkylamino, pyranyl, tetrahydropyranyl, pyridyl, $C_1-C_4$-alkylpyridyl, pyrrolidinyl, piperidinyl, N-$C_1-C_4$-alkylpiperidinyl, $C_1-C_4$-alkylcyclopropyl, or di-$C_1-C_4$-alkyldioxolanyl, B is hydrogen, and for the case in which $A=COOR^3$, providing however that $R^3$ is not hydrogen, also $COR^8$ or $SO_2R^9$, $R^8$ is $C_1-C_8$-alkyl, $C_1-C_6$-halogenalkyl, or phenyl, if necessary substituted one or more times by halogen, nitro, methyl or methoxy, and $R^9$ is $C_1-C_6$-alkyl, trifluoromethyl, trichloromethyl or phenyl, if necessary substituted by halogen, nitro or $C_1-C_6$-alkyl, displays, in surprising manner, a greater herbicidal effectiveness, or an improved selectivity, compared with the known compounds.

The compounds according to the invention of general Formula I can be manufactured, for example, by the following steps:

(A) for the case in which $A=COOH$ and $B=$hydrogen, cyclicizing a compound of general Formula II

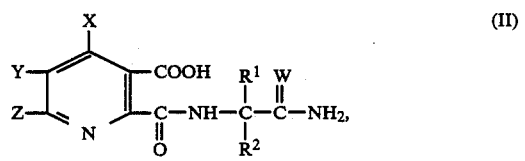

in which $R^1$, $R^2$, W, X, Y and Z have the same meanings as for formula I given above, under alkaline conditions;

(B) for the case in which $A=COOR^3$, but $R^3$ is not hydrogen, and $B=$hydrogen, reacting a compound of the general formula III

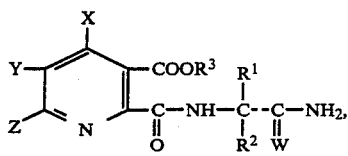

in which $R^1$, $R^2$, $R^3$, W, X, Y and Z have the same meanings as for formula I, providing that $R^3$ is not hydrogen, with a mixture of phosphoroxychloride and phosphorpentachloride, (C) for the case in which A=COOR$^3$, but $R^3$ is not hydrogen, CONR$^4$R$^5$ or CH$_2$OH, and B is hydrogen, reacting an imidazopyrrolopyridine of the general formula IV

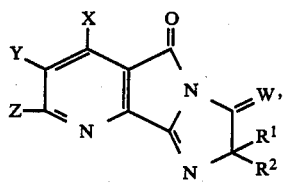

in which $R^1$, $R^2$, W, X, Y and Z have the same meanings as for general formula I, (C1) with an alcohol of the general formula

in which $R^3$ has the same meaning as for general formula I, but is not hydrogen, and the corresponding alkali metal alkoxide, if necessary in the presence of a solvent, or (C2) with an amine of the general formula

HNR$^4$R$^5$, in which $R^4$ and $R^5$ have the same meanings as for general formula I, if necessary with employment of a solvent, or (C3) with a reducing agent, such as sodium borohydride, (D) for the case in which A=COOH, reacting a compound of the general formula V

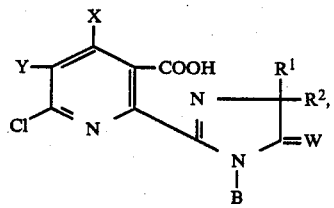

in which B, $R^1$, $R^2$, W, X and Y have the same meanings as for general formula I, with a compound of the general formula

ZH, whereby Z has the same meaning as for general formula I, or a compound of general formula XI

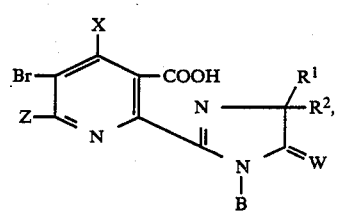

in which X, Z, B, $R^1$, $R^2$ and W have the same meaning as for general formula I, with a compound of formula YH, whereby Y has the same meaning as for formula I, (E) for the case in which $R^6$ or $R^7$ in substituents Y or Z are not hydrogen, alkylating a compound of the general formula I, in which A, B, $R^1$, $R^2$, W, X, Y and Z have the same meanings as for general formula I, however with Y or Z representing an SH- or OH-group, (F) if desired, converting a compound of general formula I obtained according to variation (A) or (D), in which $R^3$ in substituent A is hydrogen, by means of reaction with an equivalent of a base as salt former, into a compound of general formula I, in which $R^3$ in substituent A is a cation, or (G) for the case in which B=COR$^8$ or SO$_2$R$^9$, reacting a compound of general formula I obtained according to process variation (B) or (C), in which A is COOR$^3$, with an acylhalogenide, acyl anhydride or sulfonyl halogenide.

Process variation (A) is expediently so performed that one treats the starting material of general formula II over a long time period, such as 0.5 to 20 hours, at a temperature in the range from 20° to 100° C., with an aqueous or even an aqueous-alcoholic alkali metal hydroxide solution, such as sodium- or potassium hydroxide solution, whereby the amount of the hydroxide, relative to the starting material of general formula II, amounts to between 2 and 10 mol-equivalents. Subsequently, the reaction mixture is cooled down, and then acidified with a strong mineral acid, such as e.g. sulfuric or hydrochloric acid.

The amide of general formula II employed as starting material can be obtained according to the following formula scheme from compounds of general formula VI, in which X, Y and Z have the same meanings as for general formula I, by means of conversion into a carboxylic acid anhydride of general formula VII, according to customary methods, and subsequently reacting with an amino acid amide of general formula VIII, in which $R^1$ and $R^2$ have the same meanings as for general formula I:

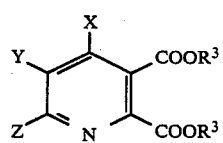

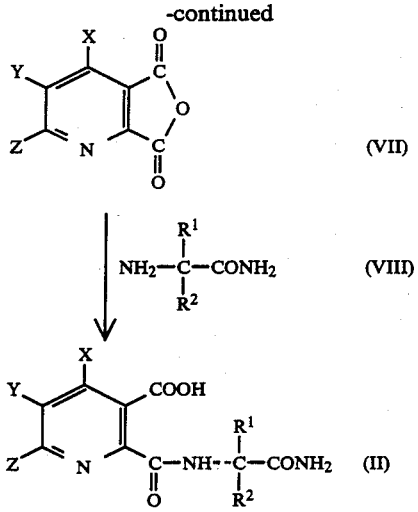

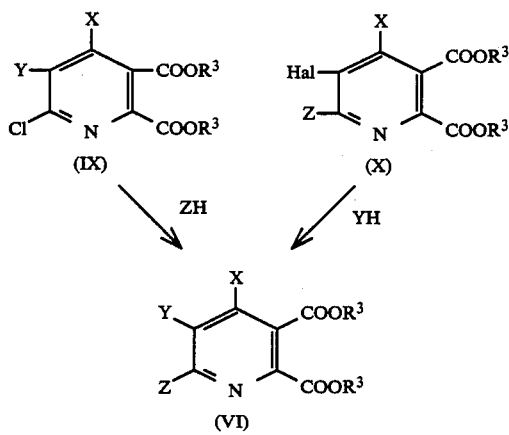

The manufacture of compounds of general formula II follows in the presence of an organic solvent, such as, for example, diethylether, tetrahydrofuran, acetonitrile or ethyl acetate, or in a halogenated solvent, such as, for example, methylene chloride or chloroform. The reaction occurs in the temperature range from 20° to 100° C. Small amounts of isomeric pyridine carboxylic acid derivatives precipitating during the reaction can easily be removed by means of recrystallization or chromatography.

The starting compounds of general formula VI are known in part, or can be obtained according to known methods. For example, 6-chloropyridine-2,3-dicarboxylic acid derivative of general formula IX (X, Y=H, $R^3$=CH$_3$, J. Chem. Soc. (B), 289–296 (1971) or 5-halogenpyridine-2,3-dicarboxylic acid derivative of general formula X (X, Z=H, Hal=Cl, $R^3$=CH$_3$; J. Med. Chem., 1067–1071 (1974) is reacted, according to the following formula scheme, with compounds of general formula YH or ZH, with X, Y, Z and $R^3$ having the same meanings as for general formula I:

The reaction follows at a temperature between 0° and 150° C., generally however between room temperature and reflux temperature of the reaction mixture. Duration of the reaction amounts to between 0.5 and 48 hours. Between 1 and 5 mol of YH or ZH are reacted, relative to the starting material, if necessary in the presence of a suitable base, such as for example, sodium hydride, sodium hydroxide, potassium hydroxide or potassium tert.-butylate. The reaction follows with or without employment of a suitable solvent, such as, for example, dimethylsulfoxide, halogen hydrocarbons, such as methylene chloride or chloroform, aromatic hydrocarbons, such as for example benzene, toluene, xylene, chlorobenzene and dichlorobenzene, acid amides, such as dimethylformamide, or other solvents inert with respect to the reaction partners, such as for example, diethylether or tetrahydrofuran.

Process variation (B) is, expediently, so performed, that the starting material of general formula III is brought to reaction directly with a mixture of phosphorpentachloride and phosphoroxychloride at room temperature.

The reaction can also be performed in the presence of a solvent inert under the reaction conditions, such as for example, toluene, xylene or chloroform, in the temperature range from 0° to 100° C. The free bases are isolated from the hydrochlorides precipitating therewith, according to typical methods, for example by reaction with sodium carbonate or with sodium hydrogen carbonate.

The starting material of general formula III is obtained from compounds of general formula II by means of esterification according to methods known per se, with the corresponding alcohols of general formula $R^3$—OH.

The process variation (C1) is, expediently, so performed, that the starting material of general formula IV is reacted with a mixture of alkali metal hydride, such as sodium hydride, and the corresponding alcohol of formula $R^3$—OH in excess, for 0.5 to 5 hours, at a temperature in the range from room temperature up to the boiling temperature of the reaction mixture. In this reaction, the employed alcohol serves not only as reactant, but also as solvent. One can, however, also employ additional solvent, such as for example, tetrahydrofuran, dioxan or other non-protic solvent.

The process variation (C2) is, expediently, so performed, that the starting material of general formula IV is reacted with a primary or secondary amine of the general formula $HNR^4R^5$, whereby $R^4$ and $R^5$ have the same meanings as for general formula I, in a temperature range from 20° to 100° C., if necessary with use of a solvent, such as for example, dimethylformamide, tetrahydrofuran or dioxan.

The process variation (C3) is, expediently, so performed, that the starting material of general formula IV is reacted with a reducing agent, such as sodium borohydride, in a temperature range from −10° to 30° C., in a suitable solvent or solvent mixture, such as for example, ethanol/tetrahydrofuran.

The starting material of general formula IV can itself be prepared from compounds of general formula I, in which A=COOH and B=hydrogen, by means of reaction with dicyclohexylcarbodiimide.

The reaction follows in an inert solvent, using an equimolar amount of the carbodiimide in a temperature range from 20° to 60° C.

The process variation (D) is, expediently, so performed, that the starting material of general formula V is reacted in a solvent with a compound Z—H, whereby Z has the same meaning as for general formula I, at a temperature between 0° and 170° C., preferably between room temperature and the boiling temperature of the reaction mixture. The reaction is terminated, depending upon the reactants, after 0.5 to 48 hours. The compounds of general formula Z—H, which represent either alcohols or mercaptans, are reacted in an amount from 1 to 5 mol-equivalents, relative to the starting material of general formula V, if necessary in the presence of a base, such as for example, sodium hydride, sodium hydroxide, potassium hydroxide or potassium tert.-butylate.

The reaction follows with or without employment of a suitable inert solvent. As suitable inert solvents, mention may be made by way of example of dimethylsulfoxide, halogen hydrocarbons, such as for example methylene chloride and chloroform, aromatic hydrocarbons, such as for example, benzene, toluene, xylene, chlorobenzene and dichlorobenzene, as well as other solvents inert with respect to the reaction partners, such as for example, diethylether, tetrahydrofuran or dimethylformamide.

The starting materials of general formula V are known in part, or can be prepared according to methods known per se from the literature.

The process variation (E) is, expediently, so performed, that a compound of general formula I, in which $R^6$ or $R^7$ is hydrogen, as starting material, is alkylated in known manner.

For this purpose, the corresponding 5-hydroxy-or 5-mercapto-, or 6-hydroxy- or 6-mercapto-derivative is reacted in a suitable solvent with an alkylation agent, preferably an alkylhalogenide, in the presence of a base, at room temperature. Suitable solvents include, for example, dimethylsulfoxide, ethers, such as for example tetrahydrofuran and dioxan, acid amides, such as dimethylformamide and dimethylacetamide, as well as acetonitrile.

The reaction proceeds, preferably, at room temperature. However, it is also possible to operate at elevated temperatures, whereby the reaction period is, naturally, shortened. As halogenides, mention may be made by way of example of the following: preferably, the chlorides, bromides and iodides. Suitable bases are alkali metal hydrides and hydroxides, such as for example, sodium hydride and potassium hydroxide.

For manufacture of compounds of general formula I according to process variation (F), in which group $R^3$ in substituents A represents a cation, one employs as starting material a compound of general formula I, in which $R^3$ is hydrogen. This is reacted in a suitable solvent, with a base as salt-former, such as for example, alkali metal- or earth alkali metal hydroxide, ammonium hydroxide or an alkylamine, such as for example, isopropylamine, expediently at room temperature.

According to process variation (G), the compounds of general formula I synthesized according to process variations (B) and (C) are reacted with an excess amount of an acylhalogenide of formula $R^8$—CO—Cl, acylanhydride of formula $R^8$—CO—O—CO—$R^8$ or sulfonylhalogenide of formula Cl—$SO_2$—$R^9$, whereby $R^8$ and $R^9$ have the same meanings as for general formula I, if necessary in the presence of a solvent such as pyridine or toluene, at a temperature between 50° and 130° C.

The compounds according to the present invention produced according to the above described process variations can be isolated from the reaction mixtures by customary techniques, for example, by casting the reaction mixture into ice water and separating the product by means of extraction with a suitable solvent or by means of filtration.

The compounds according to the present invention represent, as a rule, crystalline or thick liquid substances, which in part are well soluble in halogenated hydrocarbons, such as chloroform, sulfoxides, such as dimethylsulfoxide, or esters, such as ethyl acetate.

The compounds provided according to the present invention display an excellent herbicidal effectiveness against economically important mono- and dicotyledonous weeds. In addition, difficultly controllable perennial weeds are well within the effective scope of the active substances.

In connection therewith, it is of no consequence whether the substances are applied in pre-sowing, pre-germination or post-germination spraying. If the compounds according to the present invention are applied to the surface of the earth before germination, the germination of the seedlings is not completely prevented. The weeds grow nearly up to the cotyledon stage, and then, however, stop growing and finally die.

The active substances according to the present invention can be employed, for example, against the following plant types:

Dicotyledonous weeds of the type Abutilon, Chrysanthemum, Brassica, Helianthus, Mentha, Sinapsis, Lepidium, Galium, Stellaria, Anthemis, Chenopidium, Atriplex, Senecia, Portulaca, Ipomoea, Matricaria, Galinsoga, Urtica, Amaranthus, Convolvulus, Polygonum, Sesbania, Ambrosia, Cirsium, Carduus, Sonchus, Solanum, Rorippa, Lamium, Veronica, Datura, Viola, Ventaurea and Galeopsis.

Monocotyledonous weeds of the types Avena, Alopecurus, Echinochloa, Setaria, Panicum, Digitaria, Poa, Eleusine, Brachiaria, Lolium, Bromus, Cyperus, Agropyron, Sagittaria, Cynodon, Monochoria, Fimbristylis, Eleocharis, Ischaemum and Apera.

The compounds can be employed in agriculturally important main cultures such as cotton, soy, rice, maize, wheat, barley, oats, sorghum and sugar beets.

The employment of the active substances according to the present invention is in no way limited to the named weed types and culture plants, but stretches in similar manner also to other plants.

The compounds are suitable, depending upon application concentration, also for total weed control, for example, at industrial and railroad plants, and at roads and other open areas such as tennis courts and the like. The compounds can likewise be employed for weed control in permanent cultures such as for example, forests, ornamental woods, orchards, vineyards, citrus stands, nut, banana, coffee, tea, rubber, oil palm, cocoa, soft fruit and hops cultures.

In other respects, the compounds display, in correspondingly lower application amounts, growth-regulatory characteristics with culture plants, in that they intervene in a regulatory manner in the plants' actual material growth, but without killing the plants, so that they can be used, for example, for general control and restraint of undesirable vegetative growth.

The employed amount of active substance can be varied over a broad range. It depends basically upon the type of the desired effect. Generally, the application amount lies between 0.01 and 5 kg active substance per hectare of ground surface. For example, in the case of weed control, it lies preferably between 0.1 and 0.5 kg active substance per hectare.

The compounds according to the present invention can be employed either alone, in mixture with one another, or in mixture with other active substances. If necessary, other plant protection or pest control agents can be added, indeed according to the desired purpose.

To the extent that a broadening of the activity spectrum is considered, other herbicides can also be added. For example, suitable as herbicidally effective mixing partners are those active substances which are set forth in Weed Abstracts, Vol. 34, Nov. 3, 1985, under the title "List of common names and abbreviations employed for currently used herbicides and plant growth regulators in Weed Abstracts".

A promotion of the intensity of activity and of the speed of activity can be obtained, for example, by means of activity-increasing additives such as organic solvents, wetting agents and oils. If necessary, such additives allow for a decrease in the dose of active substance.

Moreover, phospholipids can be employed as mixing partners, for example those from the groups phosphatidylcholine, the hydrated phosphatidyl cholines, phosphatidyl ethanolamine, the N-acyl-phosphatidyl ethanolamines, phosphatidyl inosite, phosphatidyl serine, lysolecithin and phosphatidyl glycerol.

Expediently, the characterized active substances or their mixtures are employed in the form of preparations such as powders, spray agents, granulates, solutions, emulsions or suspensions, with addition of liquid and/or solid carrier substances or diluting agents, and, if necessary, adhering, wetting, emulsifying and/or dispersing adjuvants.

Suitable liquid carrier substances include, for example, aliphatic and aromatic hydrocarbons such as benzene, toluene, xylene, cyclohexanone, isophoron, dimethylsulfoxide, dimethylformamide, moreover mineral oil fractions and plant oils.

Suitable as solid carrier materials are minerals, for example Bentonite, silica gel, talc, kaolin, Attapulgite, limestone, and plant products, for example meal.

As surface-active substances, mention may be made by way of example of calcium lignin sulfonate, polyethylene alkylphenylether, naphthaline sulfonic acids and their salts, phenol sulfonic acids and their salts, formaldehyde condensate, fatty alcohol sulfate, as well as substituted benzene sulfonic acids and their salts.

The portion of active substances in the various preparations can vary within broad limits. For example, the compositions can contain about 10 to 90% by weight of active substance, about 90 to 10% by weight of liquid or solid carrier substance as well as, if necessary, up to 20% by weight of surface-active substance, upon corresponding reduction in the amount of carrier material.

The application of the compositions can follow in customary manner, for example with water as carrier in spray brew amounts of about 100 to 1000 liter/ha. An application of the compositions in the so-called low volume and ultra-low volume techniques is likewise possible, as is their application in the form of so-called microgranulates.

The manufacture of these preparations can be performed in a manner known per se, for example by means of milling or mixing techniques. If desired, preparations of the individual components can also be mixed first briefly before their employment, such as performed, for example, in the so-called tank mixing technique in practice.

For manufacture of the various preparations, the following components, for example, can be employed:

(A) SPRAY POWDER (1)

80% by weight active substance
15% by weight kaolin
5% by weight surface-active substance based upon the sodium salt of N-methyl-N-oleyl-taurine and the calcium salt of lignin sulfonic acid (2)

20% by weight active substance
35% by weight Bentonite
8% by weight calcium salt of lignin sulfonic acid
2% by weight sodium salt of N-methyl-N-oleyl-taurine
35% by weight silicic acid

(B) PASTE

45% by weight active substance
5% by weight sodium aluminum silicate
15% by weight cetylpolyglycolether with 8 mol ethylene oxide
2% by weight spindle oil
10% by weight polyethylene glycol
23% by weight water

(C) EMULSION CONCENTRATE

20% by weight active substance
50% by weight cyclohexanone
25% by weight aromatic hydrocarbon
5% by weight combination emulsifier of calcium dodecylbenzene sulfonate and nonylphenol polyglycolether The following non-limiting examples should more fully set forth the generic and specific details of the invention.

DESCRIPTION OF THE PREFERRED EMBODIMENTS

EXAMPLE 1

(Process Variation A)

6-benzylthio-2-(4-isopropyl-4-methyl-5-oxo-2-imidazolin-2-yl)-nicotinic acid 7.5 g (0.028 mol) 6-benzylthiopyridine-2,3-dicarboxylic acid anhydride are saturated with 30 ml acetonitrile and reacted, under stirring, with a solution of 3.6 g (0.028 mol) 2-methyl-valinamide in 20 ml acetonitrile. After 15 minutes, it is compressed, and the formed 6-benzylthio-2-(N-1-carbamoyl-1,2-dimethylpropyl-carbamoyl)-nicotinic acid is reacted with 50 ml of 2.6N sodium hydroxide and heated for 6 hours under stirring to 100° C. This is then acidified at room temperature with concentrated hydrochloric acid, extracted with methylene chloride, dried over magnesium sulfate and compressed.

Yield: 3.6 g (33.5% of theoretical amount)
MP: 190° C.

The starting material is prepared as follows:

6-benzylthiopyridine-2,3-dicarboxylic acid dimethyl ester 3.7 g (0.03 mol) benzylmercaptan are added to a mixture of 8.3 g (0.06 mol) potassium carbonate in 20 ml dimethylformamide and stirred 10 minutes. Then, 6.9 g (0.03 mol) 6-chloropyridine-2,3-dicarboxylic acid dimethyl ester are added, and the reaction mixture is stirred for 6 hours at 100° C. After cooling down to room temperature, the reaction mixture is cast into ice water, the product is extracted with methylene chloride, the organic phase is washed with dilute hydrochloric acid and water, dried across magnesium sulfate and rotated. The product crystallizes from the oily residue.

Yield: 7.3 g (76.8% of theoretical amount)
MP: 80°–84° C.

6-benzylthiopyridine-2,3-dicarboxylic acid 15.0 g (0.375 mol) sodium hydroxide are dissolved in 40 ml water and added to a stirred mixture of 7.3 g (0.023 mol) 6-benzylthiopyridine-2,3-dicarboxylic acid dimethyl ester in 40 ml ether. It is stirred for 4 hours at 40° C., the aqueous phase is acidified with concentrated hydrochloric acid, and the product is extracted with ethyl acetate, the solvent then being dried across magnesium sulfate and compressed. The product crystallizes from the residue.

Yield: 6.36 g (95.6% of theoretical amount)
MP: 175° C.

6-benzylthio-pyridine-2,3-dicarboxylic acid anhydride 8.5 g (0.029 mol) 6-benzylthiopyridine-2,3-dicarboxylic acid are stirred into 150 ml acetanhydride 6 hours at 110° C. The substance thereby dissolves completely. The solvent is distilled off in a vacuum and the residue is employed in the next stage without further purification.

Yield: 7.5 g (78.6% of theoretical amount)

EXAMPLE 2

(Process Variation F)

6-benzylthio-2-(4-isopropyl-4-methyl-5-oxo-2-imidazolin-2-yl)-nicotinic acid, isopropyl ammonium salt 0.16 g (2.7 mmol) isopropylamine are added to a solution of 1.0 g (2.7 mmol) 6-benzylthio-2-(4-isopropyl-4-methyl-5-oxo-2-imidazolin-2-yl)-nicotinic acid in 50 ml ether and 50 ml tetrahydrofuran. The sediment is sucked off and dried.

Yield: 0.93 g (80.75% of theoretical amount)
MP: 174°–175° C.

EXAMPLE 3

(Process Variation B)

5-hydroxy-2-(4-isopropyl-4-methyl-5-oxo-2-imidazolin-2-yl)-6-methyl-nicotinic acid methyl ester A solution of 47 g (0.129 mol) 5-acetoxy-2-(1-carbamoyl-1,2-dimethylpropyl-carbamoyl)-6-methyl-nicotinic acid methyl ester and 93.8 g phosphorus pentachloride in 470 ml phosphoroxychloride is stirred 12 hours at room temperature. The solution is then hydrolysed with ice and neutralized with sodium carbonate. The product is extracted with ethyl acetate, the extract is then dried across magnesium sulfate and compressed. The crude product is recrystallized from ethyl acetate/isopropyl ester.

Yield: 22 g (55.9% of theoretical amount)
MP: 206° C.

The starting material is prepared as follows:

5-acetoxy-6-methyl-pyridine-2,3-dicarboxylic acid anhydride

A suspension of 1.0 g (5.1 mmol) 5-hydroxy-6-methylpyridine-2,3-dicarboxylic acid and 5 ml acetic acid anhydride are heated at a bath temperature of 140° C. until a clear solution is produced. After compressing, the desired product is obtained.

Yield: 1.1 g (97.5% of theoretical amount)
MP: 123°–125° C.

5-acetoxy-2-(1-carbamoyl-1,2-dimethylpropyl-carbamoyl)-6-methyl-nicotinic acid 6.3 g (28.48 mmol) 5-acetoxy-6-methyl-pyridine-2,3-dicarboxylic acid anhydride and 4.1 g (31.33 mmol) 2-methyl-valinamide are stirred under nitrogen for 2 days at room temperature, and then the precipitated crystalline product is filtered off.

Yield: 9.5 g (95% of theoretical amount)
MP: about 143° C.

5-acetoxy-2-(1-carbamoyl-1,2-dimethylpropyl-carbamoyl)-6-methyl-nicotinic acid methyl ester Hydrochloric acid gas is led for 3 hours through a solution of 53 g (0.151 mol) 5-acetoxy-2-(1-carbamoyl-1,2-dimethylpropyl-carbamoyl)-6-methyl-nicotinic acid in 500 ml absolute methanol boiling under reflux. Then, the solvent is evaporated and the product is dried in a vacuum.

Yield: 47.1 g (85.5% of theoretical amount)
MP: 145° C. (decomposition)

EXAMPLE 4

(Process Variation C)

6-benzylthio-2-(4-isopropyl-4-methyl-5-oxo-2-imidazolin-2-yl)-nicotinic acid methyl ester 4.0 g (0.011 mol) 2-isopropyl-2-methyl-5H-imidazo (1',2':1,2)-pyrrolo(3,4-b)-2-benzylthiopyridine-3(2H)-5-dion is added to a mixture of 0.2 g sodium hydride in 40 ml methanol and heated under reflux for 2 hours. The mixture is then cast into ice water after cooling down, and the product is extracted with chloroform.

Yield: 2.7 g (61.8% of theoretical amount)
MP: 157°–158° C.

The starting material is prepared as follows:

2-isopropyl-2-methyl-5H-imidazo(1',2':1,2)-pyrrolo(3,4-b)-2-benzylthiopyridine-3(2H)-5-dion 1.0 (0.005 mol) dicyclohexylcarbodiimide and 2.0 g (0.005 mol) 6-benzylthio-2-(4-isopropyl-4-methyl-5-oxo-2-imidazolin-2-yl)-nicotinic acid are dissolved in 30 ml methylene chloride, then stirred for 4 hours at room temperature and allowed to stand overnight. The reaction mixture is filtered and the filtrate is then compressed. The oily residue crystallizes after a while.

Yield: 1.7 g (93.4% of theoretical amount)
MP: 155°–157° C.

EXAMPLE 5

(Process Variation D)

2-(4-isopropyl-4-methyl-5-oxo-2-imidazolin-2-yl)-6-tetrahydrofurfuryloxy-nicotinic acid 1.0 ml (0.01 mol) tetrahydrofurfuryl alcohol are added to a mixture of 1.0 g (0.033 mol) sodium hydride (80%) in 10 ml dimethylformamide and after-stirred for 1 hour. Then, 2.95 g (0.01 mol) 6-chloro-2-(4-isopropyl-4-methyl-5-oxo-2-imidazolin-2-yl)-nicotinic acid, dissolved in 10 ml dimethylformamide, are added dropwise. The mixture is then stirred for 1 hour at 50°–60° C., cooled to room temperature, then 10 ml water is added, followed by acidifying with concentrated hydrochloric acid. The product is extracted with methylene chloride, the extract is dried across magnesium sulfate, filtered and compressed. After a certain period the product crystallizes from the obtained oil.
- Yield: 1.8 g (50% of theoretical amount)
 MP: 155°–160° C.

EXAMPLE 6

(Process Variation E)

2-(4-isopropyl-4-methyl-5-oxo-2-imidazolin-2-yl)-6-methyl-5-methylthiomethoxy-nicotinic acid methyl ester A solution of 2.5 g (8.19 mmol) 5-hydroxy-2-(4-isopropyl-4-methyl-5-oxo-2-imidazolin-2-yl)-6-methyl-nicotinic acid methyl ester in 25 ml dimethyl sulfoxide is reacted with 0.26 g (8.19 mmol) sodium hydride (80%) and after 10 minutes' stirring, 0.87 g (9.01 mmol) chlorodimethylsulfide is added. It is stirred overnight, then added to 500 ml ice water. The product is extracted with ethyl acetate, the extract is dried over magnesium sulfate, and compressed. The residue is chromatographed over silica gel with ethyl acetate/hexane 1:1.

Yield: 0.53 g (17.7% of theoretical amount)
MP: 96°–98° C.

In analogous manner, the compounds set forth by way of formula in the following table are prepared according to the designated process variation:

TABLE

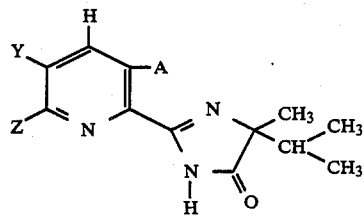

| Example No. | Y | Z | A | MP. (°C.) | Process Var'n |
|---|---|---|---|---|---|
| 7 | H | S—(CH2)4CH3 | COOH | 105–108 | D |
| 8 | H | S—(CH2)4CH3 | COOH × NH2—i-Pr | oil | F |
| 9 | H | S-(2-pyridyl) | COOH | 155 | D |
| 10 | H | S-(2-pyridyl) | COOH × NH2—i-Pr | 91–95 | F |
| 11 | H | O—CH2-(2-furyl) | COOH | 208 | D |
| 12 | H | O—CH2-(2,2-dimethyl-1,3-dioxolan) | COOH | 164 | D |
| 13 | H | S—(CH2)3Ph | COOH × H2O | 150 | D |
| 14 | H | S—CH2—Ph | COOC2H5 | 126–128 | C |
| 15 | H | S—CH2—Ph | COO—i-C3H7 | 175–177 | C |
| 16 | H | S—CH2—Ph | COO—CH2-(tetrahydrofuryl) | 100 | C |
| 17 | H | S—CH2—Ph | COO—CH2-(2-furyl) | 138 | C |
| 18 | H | S—CH2—Ph | COO-butyl | 140 | C |

TABLE-continued

| Example No. | Y | Z | A | MP. (°C.) | Process Var'n |
|---|---|---|---|---|---|
| 19 | H | S—CH₂—(3,4-dichlorophenyl) | COOH | 171 | D |
| 20 | H | S—(4-fluorophenyl) | COOH | 161 | D |
| 21 | H | S—CH₂—CH=CH₂ | COOH | 155–160 | D |
| 22 | H | S—CH₂—(2-furyl) | COOH | 170–180 | D |
| 23 | H | S—cyclohexyl | COOH | 125–129 | D |
| 24 | H | S—phenyl | COOH | 136 | D |
| 25 | H | S—(CH₂)₂Ph | COOH | 122 | D |
| 26 | H | S—(CH₂)₂—CH(CH₃)₂ | COOH | 120 | D |
| 27 | H | S—(3-methylphenyl) | COOH | 115 | D |
| 28 | H | S—(4-methylphenyl) | COOH | 120 | D |
| 29 | H | S—(4-chlorophenyl) | COOH | 158 | D |
| 30 | H | S—(CH₂)₂—OH | COOH | 180 | D |
| 31 | H | O—CH₂—cyclopropyl | COOH | 170 | D |
| 32 | H | O—CH₂—(1,3-dioxolan-2-yl) | COOH | 130 | D |

TABLE-continued

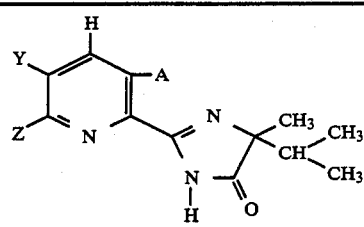

| Example No. | Y | Z | A | MP. (°C.) | Process Var'n |
|---|---|---|---|---|---|
| 33 | H | O—CH₂—cyclohexyl | COOH | 142 | D |
| 34 | H | O—CH₂—(tetrahydropyran-2-yl) | COOH | 180 | D |
| 35 | H | SH | COOH | 175/dec. | |
| 36 | H | S—CH₂—phenyl | CONH₂ | 198–204 | C |
| 37 | H | S—CH₂—phenyl | CONHNH₂ | >250 | C |
| 38 | H | S—CH₂—(4-chlorophenyl) | COOH | 130–140 | D |
| 39 | H | S—CH₂—(tetrahydrofuran-2-yl) | COOH | 95 | D |
| 40 | H | S—CH₂—cyclopropyl | COOH | 140 | D |
| 41 | CH₃ | O—CH₂—S—CH₃ | COOH | 146–150 | E |
| 42 | H | S—cyclopentyl | COOH | 196 | D |
| 43 | H | O—CH₂—(tetrahydrofuran-2-yl) | COOH × H₂N—CH(CH₃)₂ | 157/dec | F |
| 44 | H | O—CH₂—cyclohexyl | COOH × H₂N—CH(CH₃)₂ | 169/dec | F |
| 45 | H | S—cyclopentyl | COOH × H₂N—CH(CH₃)₂ | 158/dec | F |

TABLE-continued

Structure: pyridine with Y, Z, A substituents connected to -C(=N-)-NH-C(=O)-C(CH₃)(CH(CH₃)₂)- (with H on position between Y and A)

| Example No. | Y | Z | A | MP. (°C.) | Process Var'n |
|---|---|---|---|---|---|
| 46 | H | cyclohexyl-S- | COOH × H₂N-C(CH₃)₃ | 167/dec | F |
| 47 | H | (1,3-dioxolan-2-yl)-CH₂-O- | COOH × H₂N-C(CH₃)₃ | 146/dec. | F |
| 48 | H | (tetrahydropyran-2-yl)-CH₂-O- | COOH × H₂N-C(CH₃)₃ | 151/dec. | F |
| 49 | H | cyclopropyl-CH₂-S- | COOH × H₂N-C(CH₃)₃ | 158/dec. | F |
| 50 | H | (tetrahydrofuran-2-yl)-CH₂-S- | COOH × H₂N-C(CH₃)₃ | 144/dec. | F |
| 51 | H | (pyridin-4-yl)-CH₂-S- | COOH | 208/dec. | D |
| 52 | phenyl-CH₂-S- | H | COOH | 112 | D |
| 53 | (tetrahydrofuran-2-yl)-CH₂-S- | H | COOH | 130 | D |
| 54 | cyclopentyl-S- | H | COOH | 141 | D |
| 55 | cyclohexyl-CH₂-O- | H | COOH | 158 | D |
| 56 | cyclopropyl-CH₂-O- | H | COOH | 110 | D |
| 57 | cyclohexyl-S- | H | COOH | 154 | D |

TABLE-continued

[Structure: pyridine ring with substituents Y, Z, A and attached imidazolinone with isopropyl and methyl groups]

| Example No. | Y | Z | A | MP. (°C.) | Process Var'n |
|---|---|---|---|---|---|
| 58 | H | O-cyclohexyl | COOH | 189–191 | D |
| 59 | H | O-cyclopentyl | COOH | 188–192 | D |
| 60 | H | O-CH₂-CH(-O-)(-O-) (dioxolane-CH₂-O-) | COOH × H₂N-iPr | 157/dec. | F |
| 61 | H | O-(tetrahydropyran-4-yl) | COOH | 145 | D |
| 62 | H | O-cycloheptyl | COOH | 140–143 | D |
| 63 | H | O-(tetrahydrofuran-3-yl) | COOH | 185 | D |
| 64 | H | O-cyclopentyl | COOH × H₂N-iPr | 182/dec. | F |
| 65 | H | O-(tetrahydrofuran-3-yl) | COOH × H₂N-iPr | 157/dec. | F |
| 66 | O-(tetrahydropyran-4-yl) | H | COOH | 150–156 | D |

EXAMPLE 7

(Process Variation D)

5-(cyclopropylmethoxy)-2-(4-isopropyl-4-methyl-5-oxo-2-imidazolin-2-yl)-nicotinic acid, hydrate 1.0 g (0.033 mol) of 80% sodium hydride is dissolved in 15 ml dimethylformamide and reacted with 1.0 g (0.015 mol) cyclopropylmethyl alcohol. Under stirring, 3.4 g (0.01 mol) 5-bromo-1-(4-isopropyl-4-methyl-5-oxo-2-imidazolin-2-yl)-nicotinic acid are added, and stirred for 2 hours at 100° C. bath temperature. After cooling down, the reaction mixture is cast onto ice, acidified with concentrated hydrochloric acid, and extracted with ethyl acetate. The organic phase is dried over magnesium sulfate, and compressed. The oily residue crystallizes from isopropylether.

Yield: 1.7 g (48.6% of theoretical amount)
MP: 105°–110° C.
RF: 0.0

The following examples serve to illustrate use possibilities of the compounds according to the present invention. They follow in the form of the above-mentioned preparations.

EXAMPLE A

In a green house, the compounds according to the present invention are sprayed onto Brassica spp. and Solanum spp. as test plants, in both pre-germination and post-germination tests, in application amounts of 3 kg active substance/ha emulsified in 100 liter water/ha. 3 weeks after the spraying treatment, the results of the treatment are classified, whereby the following scheme is employed:
0=no activity
1=low activity or weak inhibition of plant growth
2=average activity or inhibition of plant growth
3=total inhibition of growth
4=total destruction of the plants It turned out that the compounds of Examples 1, 2, 5–8, 11–13, 19–26, 33–59, and 66 caused in these tests a 100% destruction (=4) of the plants.

EXAMPLE B

In a greenhouse, the indicated plants are treated before germination with the compounds to be tested in an application amount of 1 kg active substance/ha. For this purpose, the compounds are sprayed over the earth, uniformly, as a suspension with 500 l water/ha. 3 weeks after the treatment, the compounds according to the present invention display a selectivity in corn with excellent activity against the weeds. The comparison agent is clearly less effective.

In the following Table, the symbols indicate:
0=no activity
1=low activity or weak inhibition of plant growth
2=average activity or inhibition of plant growth
3=total inhibition of growth
4=total destruction of plants
Ze=Zea mays
Br=Brassica sp.
So=Solanum sp.
Me=Medicago sp.
He=Helianthus sp.
St=Stellaria sp.
Ab=Abutilon sp.
Ma=Matricaria sp.
Vi=Viola sp.
Ch=Chrysanthemum sp.
Sr=Sorghum sp.
Av=Avena sp.
Al=Alopecurus sp.
Ec=Echinochloa sp.
Se=Setaria sp.
Cy=Cyperus sp.

EXAMPLE C

In a greenhouse, the plants indicated are treated before germination with the compounds set forth in an application amount of 1 kg active substance/ha. For this purpose, the compounds are sprayed uniformly over the earth as a suspension with 500 l water/ha. 3 weeks after the treatment, the compounds according to the present invention display a selectivity in soy (Glycine max.) with excellent activity against the weeds.

Symbols in the following Table mean:
0=no activity
1=low activity or weak inhibition of plant growth
2=average activity or inhibition of plant growth
3=total inhibition of growth
4=total destruction of the plants
Gl=Glycine max.
Br=Brassica sp.
So=Solanum sp.
Me=Medicago sp.
He=Helianthus sp.
St=Stellaria sp.
Ma=Matricaria sp.
Ch=Chrysanthemum sp.
Se=Setaria sp.

| Compounds According To The Invention | Gl | Br | So | Me | He | St | Ma | Ch | Se |
|---|---|---|---|---|---|---|---|---|---|
| Example 58 | 0 | 4 | 4 | 4 | 4 | 4 | 4 | 4 | 4 |
| Example 59 | 0 | 4 | 4 | 4 | 4 | 4 | 4 | 4 | 4 |

It will be understood that each of the elements described above, or two or more together, may also be used in other types of plant applications differing from the types described above.

While the invention has been described and illustrated as embodied in Imidazolinyl derivatives, processes for the production of these compounds as well as compositions containing the same having herbicidal activity, it is not intended to be limited to the details shown, since various modifications and changes may be made without departing in any way from the spirit of the present invention.

Without further ado, the foregoing will so fully reveal the gist of the present invention, that others can, without undue experimentation, practice the same, without omitting features that, from the standpoint of prior art, fairly constitute the generic and specific aspects of this invention.

| Compounds According To The Invention | Ze | Br | So | Me | He | St | Ab | Ma | Vi | Ch | Sr | Av | Al | Ec | Se | Cy |
|---|---|---|---|---|---|---|---|---|---|---|---|---|---|---|---|---|
| Example 5 | 0 | 3 | 3 | 3 | 3 | 3 | 4 | 4 | 3 | 3 | 4 | 4 | 4 | 4 | 4 | 4 |
| Example 12 | 0 | 3 | 3 | 3 | 3 | 3 | 3 | 4 | 3 | 3 | 3 | 3 | 3 | 3 | 4 | 3 |
| Comparison Agent (according to DE-OS 31 21 736) 6-butylthio-2-(4-isopropyl-4-methyl-5-oxo-2-imidazolin-2-yl)-nicotinic acid | 0 | 2 | 2 | 0 | 1 | 0 | 2 | 4 | 2 | 1 | 0 | 1 | 1 | 0 | 1 | 2 |

What is desired to be protected by Letters Patent is set forth in the following claims.

We claim:
1. 2-(2-imidazolin-2-yl)-pyridin-3-carboxylic acid derivative of the formula I

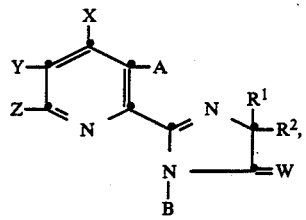

in which
$R^1$ is $C_1-C_4$-alkyl,
$R^2$ is $C_1-C_6$-alkyl or $C_3-C_6$-cycloalkyl, or
$R^1$ and $R^2$ together with the adjacent carbon atom are $C_3-C_6$-cycloalkyl or $C_3-C_6$-cycloalkyl substituted by methyl,
W is an oxygen atom or a sulfur atom,
A is one of the groups $CH_2OH$, $COOR^3$ or $CONR^4R^5$,
$R^3$ is hydrogen, $C_1-C_{12}$-alkyl, $C_2-C_{12}$-alkyl interrupted by one or more oxygen or sulfur atoms, $C_1-C_{12}$-alkyl substituted by $C_1-C_3$-alkoxy, halogen, hydroxy, $C_3-C_6$-cycloalkyl, benzyl, furyl, tetrahydrofuryl, phenyl, halogenphenyl, $C_1-C_4$-alkylphenyl, $C_1-C_4$-alkoxyphenyl, nitrophenyl, cyano, carboxyl, $C_1-C_4$-alkoxycarbonyl or $C_1-C_4$-alkylthio, $C_3-C_8$-alkenyl, $C_3-C_8$-alkenyl substituted by $C_1-C_3$-alkoxy, phenyl or halogen, $C_3-C_8$-alkinyl, $C_3-C_8$-alkinyl substituted by $C_1-C_3$-alkoxy, phenyl or halogen, $C_3-C_6$-cycloalkyl, $C_3-C_6$-cycloalkyl substituted by methyl, or a cation selected from the group consisting of alkali metals, alkali earth metals, manganese, copper, iron, zinc, ammonium and organic ammonium compounds,
$R^4$ and $R^5$ are the same or different and are each hydrogen, hydroxy or $C_1-C_4$-alkyl, and for the case in which $R^4$ is hydrogen, $R^5$ is also amino, dimethylamino, acetylamino or anilino, X is hydrogen, nitro, $C_1-C_3$-alkyl, $C_1-C_3$-halogenalkyl or $C_1-C_3$-alkoxy, and
one of groups Y and Z is $SR^6$ or $OR^7$, while the other of groups Y and Z is hydrogen, halogen, $C_1-C_4$-alkyl, $C_1-C_4$-halogenalkyl, $C_1-C_4$-alkoxy or $C_1-C_4$-alkylthio,
$R^6$ is halogenphenyl, di-$C_1-C_3$-alkylphenyl, nitrophenyl, $C_1-C_3$-alkoxyphenyl, pyridyl, $C_1-C_3$-alkyl-pyridyl, $C_2-C_8$-alkyl interrupted by oxygen, $C_3-C_8$-cycloalkyl,
$R^7$ is $C_3-C_8$-cycloalkyl, $C_3-C_8$-cycloalkyl substituted by $C_1-C_4$-alkyl, $C_1-C_4$-alkoxy or halogen, $C_5-C_8$-cycloalkenyl,
B is hydrogen, and for the case in which $A=COOR^3$, with the proviso that $R^3$ is not hydrogen, B is also $COR^8$ or $SO_2R^9$, $R^8$ is $C_1-C_8$-alkyl, $C_1-C_6$-halogenalkyl, phenyl or phenyl substituted one or more times the same or differently by halogen, nitro, methyl or methoxy and
$R^9$ is $C_1-C_6$-alkyl, trifluoromethyl, trichloromethyl, phenyl or phenyl substituted by halogen, nitro or $C_1-C_6$-alkyl.

* * * * *